(12) United States Patent
Berge et al.

(10) Patent No.: US 7,030,137 B2
(45) Date of Patent: Apr. 18, 2006

(54) SUBSTITUTED THIOPHENES WITH ANTIBACTERIAL ACTIVITY

(75) Inventors: John Berge, Harlow (GB); Richard Jarvest, Stevenage (GB); Catherine Simone Victoire Frydrych, Harlow (GB); Joseph Guiles, Lafayette, CO (US); Jian Qiu, Longmont, CO (US); Theodore M. Tarasow, Longmont, CO (US)

(73) Assignee: Replidyne, Inc., Louisville, CO (US)

( * ) Notice: Subject to any disclaimer, the term of this patent is extended or adjusted under 35 U.S.C. 154(b) by 0 days.

(21) Appl. No.: 10/789,811

(22) Filed: Feb. 27, 2004

(65) Prior Publication Data

US 2005/0009833 A1    Jan. 13, 2005

Related U.S. Application Data

(60) Provisional application No. 60/527,229, filed on Dec. 5, 2003.

(51) Int. Cl.
    *A61K 31/4709*    (2006.01)
    *C07D 215/38*    (2006.01)
    *C07D 409/12*    (2006.01)

(52) U.S. Cl. .................. 514/312; 514/313; 546/153; 546/159

(58) Field of Classification Search ............... 546/153, 546/163; 514/312, 313
See application file for complete search history.

(56) References Cited

U.S. PATENT DOCUMENTS 6,320,051 B1    11/2001    Berge et al.

FOREIGN PATENT DOCUMENTS

| EP | 0 785 268 | 7/1997 |
|---|---|---|
| WO | WO 00/71522 | 11/2000 |
| WO | WO 00/71524 | 11/2000 |

OTHER PUBLICATIONS

Fleischmann et al. (1995) Science 269:496-512.
Gutschow (1996) J. Het. Chem. 33:355-360.
Lespagnol et al. (1968) Ann Pharm Fr. 26(3):207-14 (and abstract in English).
Jarvest et al. (2002) J. Med. Chem. 45:1959.

*Primary Examiner*—Bernard Dentz
(74) *Attorney, Agent, or Firm*—Swanson & Bratschun, LLC

(57) ABSTRACT

Novel substituted thiophenes that are inhibitors of bacterial methionyl t-RNA synthetase (MRS) are disclosed. Also disclosed are method for their preparation and their use in therapy as anti-bacterial agents.

27 Claims, No Drawings

SUBSTITUTED THIOPHENES WITH ANTIBACTERIAL ACTIVITY

CROSS-REFERENCE TO RELATED APPLICATIONS

This application claims the benefit of U.S. Provisional Application No. 60/527,229, entitled Substituted Thiophenes with Antibacterial Activity, filed Dec. 5, 2003 and also claims the benefit of United Kingdom Patent Application No. 0304809.7, entitled Novel Compounds, filed Mar. 3, 2003.

FIELD OF THE INVENTION

The present invention relates to novel substituted thiophenes that are inhibitors of bacterial methionyl t-RNA synthetase (MRS), processes for their preparation and their use in therapy as anti-bacterial agents.

BACKGROUND OF THE INVENTION t-RNA synthetases are involved in protein biosynthesis so that inhibition thereof may be expected to lead to a cessation of cell growth. Thus, for instance, the compound mupirocin, produced by the organism *Pseudomonas fluorescens*, is an anti-bacterial agent and is used as the active ingredient in the product Bactroban, marketed by GlaxoSmithKline. Mupirocin has been shown to be an inhibitor of the isoleucyl t-RNA synthetase. Each t-RNA synthetase represents a separate target for drug discovery. t-RNA synthetase inhibitors which are selective for bacterial cells over mammalian cells are of considerable therapeutic interest as they have the potential to be used as anti-bacterial agents.

The sequence of the t-RNA synthetase genes in the Gram positive organism *S aureus* have recently been determined (see, for instance, European Patent application no 97300317.1, SmithKline Beecham, for *S aureus* MRS), thereby assisting the process of identifying inhibitors. In addition, the sequence of t-RNA synthetase genes in other pathogenic bacteria, for instance the Gram negative organism *H influenzae*, has also been published (R. D. Fleischmann et al., Science, 269, 496–512, 1995).

Lespagnol et al have described a group of 8-substituted theophylline derivatives, in particular 8-[2-(benzylamino) ethylamino]theophylline, which have hypotensive activity (Ann Pharm Fr, 1968, 26(3), 207–14).

The disclosure of all patents, patent application publications, and other references referred to herein is incorporated by reference herein in their entirety.

DETAILED DESCRIPTION OF THE INVENTION

We have now found a novel class of substituted thiophenes that are potent inhibitors of bacterial methionyl t-RNA synthetase.

The invention provides compounds of the formula (I):

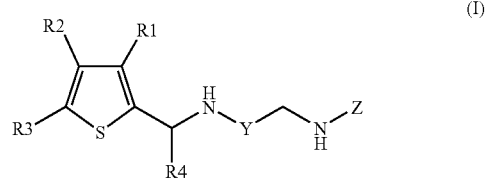

in which
$R^1$ is selected from the group consisting of $C_{(1-3)}$alkyl, $C_{(2-3)}$ alkenyl, $C_{(2-3)}$ alkynyl;
$R^2$ is a halogen, preferably Br;
$R^3$ is selected from the group consisting of Br, optionally fluoro-substituted $C_{(1-3)}$ alkyl, optionally fluoro-substituted $C_{(2-3)}$ alkenyl, and $C_{(2-3)}$ alkynyl;
$R^4$ is selected from the group consisting of H, and $C_{(1-3)}$ alkyl;
Y is $C_{(1-3)}$ alkyl; and
Z is selected from the group consisting of substituted or unsubstituted heteroaryl imidiazole, substituted or unsubstituted quinolone, substituted or unsubstituted benzimidazole, substituted or unsubstituted fused heteroaryl pyridone, substituted or unsubstituted fused aryl pyrimidone, or substituted or unsubstituted fused heteroaryl pyrimidone.

The preferred embodiments of the invention are those compounds wherein:
$R^1$ is selected from the group consisting of methyl, allyl, propene, and propyne;
$R^2$ is Br;
$R^3$ is selected from the group consisting of Br, ethyl, cyclopropyl, difluoromethyl, trifluoromethyl, vinyl, fluorovinyl, and ethyne;
$R^4$ is H;
Y is $C_2$ alkyl; and
Z is selected from the group consisting of quinoline, heteroaryl imidazole, benzimidazole, and heteroaryl pyrimidone.

Compounds of formula (I) are inhibitors of bacterial methionyl tRNA synthetase.

Salts may be formed from inorganic and organic acids. Representative examples of suitable inorganic and organic acids from which pharmaceutically acceptable salts of compounds of formula (I) may be formed include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

When used herein, the term "alkyl" and similar terms such as "alkoxy" includes all straight chain, branched, and cyclic isomers. Representative examples thereof include methyl, ethyl, n-propyl, iso-propyl, cyclopropyl, n-butyl, sec-butyl, iso-butyl, t-butyl, n-pentyl and n-hexyl. Optionally fluoro-substituted alkyls may have 1 or more substitutions of F for H on the alkyl chain. A representative example of an optionally fluorosubstituted alkyl is trifluoromethyl.

When used herein, the terms "alkenyl" and "alkynyl" include all straight chain, branched and cyclic isomers. Representative examples thereof include vinyl, ethynyl and 1-propynyl. Optionally fluorosubstituted alkenyls may have 1 or more substitutions of F for H on the alkenyl chain. A representative example of an optionally fluorosubstituted alkenyl is fluorovinyl.

Preferred substituents for alkyl and alkenyl groups include, for example, and unless otherwise defined, halogen, cyano, azido, nitro, carboxy, $(C_{1-6})$alkoxycarbonyl, carbamoyl, mono- or di-$(C_{1-6})$alkylcarbamoyl, sulpho, sulphamoyl, mono- or di-$(C_{1-6})$alkylsulphamoyl, amino, mono- or di-$(C_{1-6})$alkylamino, acylamino, ureido, $(C_{1-6})$alkoxycarbonylamino, 2,2,2-trichloroethoxycarbonylamino, aryl, heterocyclyl, hydroxy, $(C_{1-6})$alkoxy, acyloxy, oxo, acyl, 2-thienoyl, $(C_{1-6})$alkylthio, $(C_{1-6})$alkylsulphinyl, $(C_{1-6})$ alkylsulphonyl, hydroxyimino, $(C_{1-6})$alkoxyimino, hydrazino, hydrazono, benzohydroximoyl, guanidino, amidino and iminoalkylamino.

When used herein, the term "aryl" includes, unless otherwise defined, phenyl or naphthyl optionally substituted with up to five, preferably up to three substituents.

When substituted, an aryl group may have up to three substituents. Preferred substituents for an aryl group include, for example, and unless otherwise defined, halogen, cyano, $(C_{1-6})$alkyl, mono to perfluoro$(C_{1-3})$alkyl, $(C_{3-7})$cycloalkyl, $(C_{2-6})$alkenyl, $(C_{1-6})$alkoxy, $(C_{2-6})$alkenoxy, arylC$_{(1-6)}$ alkoxy, halo$(C_{1-6})$alkyl, hydroxy, amino, mono- or di-$(C_{1-6})$alkylamino, acylamino, nitro, carboxy, $(C_{1-6})$alkoxycarbonyl, $(C_{1-6})$alkenyloxycarbonyl, $(C_{1-6})$alkoxycarbonyl$(C_{1-6})$alkyl, carboxy$(C_{1-6})$alkyl, $(C_{1-6})$alkylcarbonyloxy, carboxy$(C_{1-6})$alkyloxy, $(C_{1-6})$alkoxycarbonyl$(C_{1-6})$alkoxy, $(C_{1-6})$alkylthio, $(C_{1-6})$alkylsulphinyl, $(C_{1-6})$alkylsulphonyl, sulphamoyl, mono- and di-$(C_{1-6})$-alkylsulphamoyl, carbamoyl, mono- and di-$(C_{1-6})$alkylcarbamoyl, and heterocyclyl.

When used herein, the term "heteroaryl" includes single or fused rings comprising up to four hetero-atoms in the ring selected from oxygen, nitrogen and sulphur. Preferably the heteroaryl ring comprises from 4 to 7, preferably 5 to 6, ring atoms. A fused heteroaryl ring system may include carbocyclic rings and need only include one heterocyclic ring.

When used herein, the term "heterocyclyl" includes aromatic and non-aromatic single or fused rings comprising up to four hetero-atoms in the ring selected from oxygen, nitrogen and sulphur. Suitably the heterocyclic ring comprises from 4 to 7, preferably 5 to 6, ring atoms. A fused heterocyclic ring system may include carbocyclic rings and need only include one heterocyclic ring.

When substituted, a heteroaryl or a heterocyclyl group may have up to three substituents. Preferred such substituents include those previously mentioned for an aryl group as well as oxo.

When used herein, the terms "halogen" and "halo" include fluorine, chlorine, bromine and iodine and fluoro, chloro, bromo and iodo, respectively.

The compounds according to the invention are suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

It will be appreciated that certain compounds of the present invention may comprise one or more chiral centres so that compounds may exist as stereoisomers, including diastereoisomers and enantiomers. The present invention covers all such stereoisomers, and mixtures thereof, including racemates.

Accordingly, the present invention provides a compound of the formula (II) when Z in formula (I) is a substituted or unsubstituted heteroaryl imidazole:

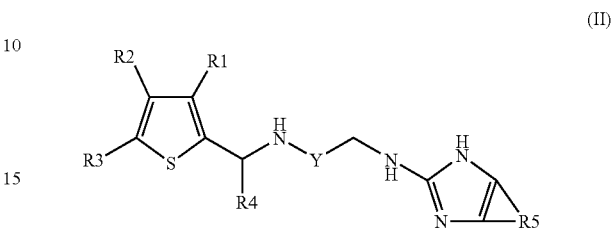

(II)

in which:
$R^1$, $R^2$, $R^3$, $R^4$ and Y are defined as in Formula (I).

$R^5$ is the residue of a 5 or 6-membered heteroaryl ring which is optionally substituted with from 1 to 3 substituents selected from halo, cyano, hydroxy, $(C_{1-6})$alkyl (optionally substituted by halo, hydroxy, amino, mono to perfluoro$(C_{1-3})$alkyl, carboxy or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy$(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heterocyclyl;

and salts thereof, preferably pharmaceutically acceptable salts thereof.

Representative heteroaryl rings formed by $R^5$ are nitrogen-containing heteroaryl rings, having 6 ring atoms and including one or two nitrogen atoms, for instance b- or c-pyrido, d-pyridimo or c-pyridazino; or sulfur-containing heteroaryl rings, having 5 ring atoms, for instance c-thieno. Preferably, the heteroaryl ring is unsubstituted. Preferably, the ring is c-pyridazino.

The present invention also provides compounds of the formula (III) when Z in formula (I) is a substituted or unsubstituted quinolone:

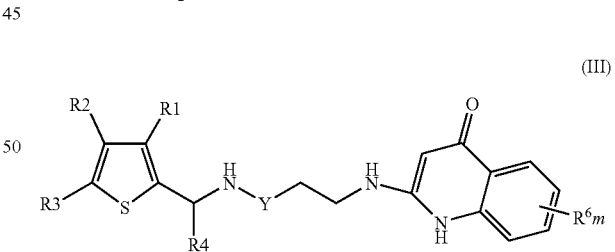

(III)

in which:
$R^1$, $R^2$, $R^3$, $R^4$ and Y are defined as in Formula (I);

$R^6$ is selected from halo, cyano, hydroxy, $(C_{1-6})$alkyl (optionally substituted by halo, hydroxy, amino, mono to perfluoro$(C_{1-3})$alkyl, carboxy or $(C_{1-6})$alkoxycarbonyl), $(C_{3-7})$cycloalkyl, $C_{(1-6)}$ alkoxy, amino, mono- or di-$(C_{1-6})$alkylamino, acylamino, carboxy, $(C_{1-6})$alkoxycarbonyl, carboxy $(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heterocyclyl;

m is 0 or an integer from 1 to 3; and salts thereof, preferably pharmaceutically acceptable salts thereof.

The present invention also provides compounds of the formula (IV) when Z in formula (I) is a substituted or unsubstituted benzimidazole:

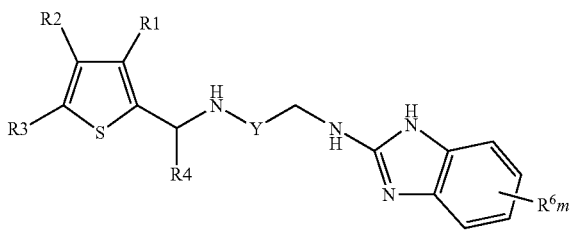

in which:

R¹, R², R³, R⁴ and Y are defined as in Formula (I);

R⁶ and m are defined as in formula (III); and salts thereof, preferably pharmaceutically acceptable salts thereof.

The present invention also provides compounds of the formula (V) when Z in formula (I) is a substituted or unsubstituted fused heteroaryl pyridone or fused heteroaryl pyrimidone:

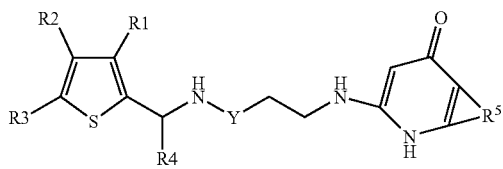

in which:

R¹, R², R³, R⁴ and Y are defined as in Formula (I);

W is CH and $R_5$ is the residue of a 5 or 6-membered heteroaryl ring, or W is N and $R_5$ is the residue of an 5 or 6-membered heteroaryl ring or an aryl ring, which heteroaryl or aryl ring is optionally substituted with from 1 to 3 substituents selected from halo, cyano, hydroxy, $(C_{1-6})$alkyl (optionally substituted by halo, hydroxy, amino, mono to perfluoro$(C_{1-3})$alkyl, carboxy or $(C_{1-6})$alkoxycarbonyl), $(C_{3-7})$cycloalkyl, $C_{(1-6)}$alkoxy, amino, mono- or di-$(C_{1-6})$alkylamino, acylamino, carboxy, $(C_{1-6})$alkoxycarbonyl, carboxy $(C_{1-6})$alkyloxy, $(C_{1-6})$alkylthio, $(C_{1-6})$alkylsulphinyl, $(C_{1-6})$alkylsulphonyl, sulphamoyl, mono- and di-$(C_{1-6})$alkylsulphamoyl, carbamoyl, mono- and di-$(C_{1-6})$alkylcarbamoyl, and heterocyclyl; and salts thereof, preferably pharmaceutically acceptable salts thereof.

Representative examples of $R_5$ when the residue of a heteroaryl ring include rings in which the heteroatom is sulphur, for instance thieno, or nitrogen, for instance pyrido, pyrimido and pyrazolo. Representative examples of $R_5$ when the residue of an aryl ring include phenyl. Representative substituents therefore include halogen, for instance chloro or bromo.

Representative examples of the moiety:

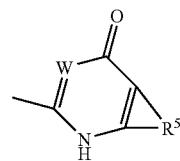

include:

W=N and $R_5$ is the residue of an aryl ring: 1H-quinazolin-4-one; W=CH and $R_5$ is the residue of a heteroaryl ring: 7H-thieno[2,3-b]pyridin-4-one, 4H-thieno[3,2-b]pyridin-7-one, 4H-thieno[3,4-b]pyridin-7-one, 1H-8,-naphthyridin-4-one; W=N and R1 is the residue of a heteroaryl ring: 1H-thieno[3,2-d]pyrimidin-4-one, 1H-thieno[2,3-d]pyrimidin-4-one, 1H-thieno[3,4-d]pyrimidin-4-one, 1Hpyrido[3,2-d]pyrimidin-4-one, 1H-pyrimido[4,5-d]pyrimidin-4-one, and 1,7-dihydropyrazolo[3,4-d]pyrimidin-4-one.

Preferably, $R_5$ forms the residue of a thieno ring.

It will be appreciated that within the compounds of formula (I) there exists a first set of pyridone compounds which W is CH, and a second set of pyrimidone compounds in which W is N, and in which $R_1$, $R_2$, $R_3$, $R_4$ and Y are as hereinbefore defined.

Preferred compounds of formula (II) include the compounds of Examples 11–21. Preferred compounds of formula (III) include the compounds of Examples 1–10. Preferred compounds of formula (IV) include the compounds of Examples 22–24. Preferred compounds of formula (V) include the compounds of Examples 25.

The compounds of formula (I) may be prepared by methods described herein or by methods described in the prior art that are incorporated by reference herein below.

A compound of formula (I) may also be prepared by reacting a compound of formula (VI):

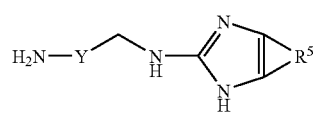

in which R⁵ and Y are as hereinbefore defined;

with either:

(a) for a compound of formula (I) in which Y is CH₂, an aldehyde of formula (VII):

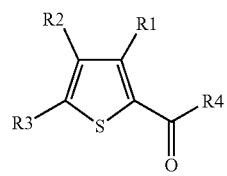

in which R¹, R², and R³ are as hereinbefore defined and R⁴=H, under reductive alkylation conditions; or (b) for a compound of formula (I) in which R⁴=alkyl as hereinbefore defined, a ketone of formula (VII): under reductive alkylation conditions.

Suitable reductive alkylating conditions are well known in the art and include for instance, the use of sodium triacetoxyborohydride in a solvent system such as DMF/acetic acid or sodium cyanoborohydride in methanol/acetic acid. Reductive alkylation with an aldehyde is typically carried out at room temperature for a period of 1–16 h. Reductive alkylation with a ketone is typically carried out in refluxing methanol for a period of 16–40 h.

A compound of formula (VI) may be prepared by reacting an imidazole compound of formula (VIII) with an amine compound of formula (IX).

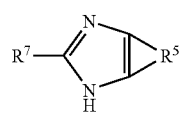
(VIII)

in which $R^5$ is as hereinbefore defined; and $R^7$ is a leaving group such as halo, for instance chloro, or $C_{(1-6)}$ alkylthio;

(IX)

in which $R^8$=H and Y was hereinbefore defined;

or an activated derivative thereof; under nucleophilic displacement conditions.

Suitable conditions are well known in the art and include the use of a large excess of the compound of formula (IX) to drive the reaction to completion and heating at a temperature of 60–130° C. Addition of a base may be advantageous in some cases, eg a tertiary base such as N,N-di(cyclohexyl)ethylamine.

A compound of formula VII may be prepared by reacting an alkyl, alkenyl, or alkyni Boronate ester X with the appropriate substituted thiophene aldehyde XI:

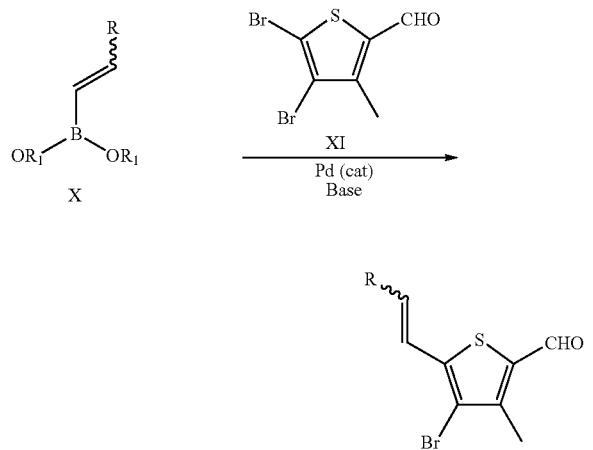

A fluorovinyl compound of formula VII may be prepared by reacting a vinylfluorosilicon derivative XII with the appropriate substituted thiophene aldehyde XI:

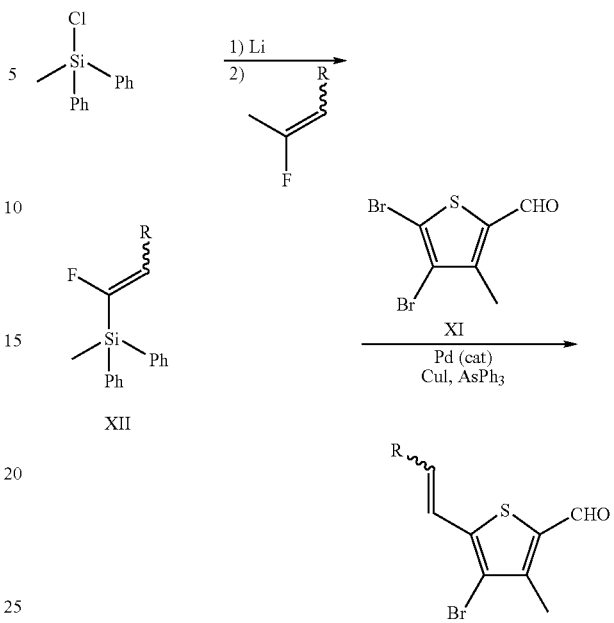

Compounds of formula (IX) are amines and are either commercially available or may be prepared form available starting materials using methods well known in the art for preparing amines, for instance by functional group interconversion Compounds of formula (II) can be prepared using methods described in U.S. Patent Application Ser. No. 60/527,229, filed on Dec. 5, 2003.

Compounds of formula (III) can be prepared using methods described in U.S. Pat. No. 6,320,051, to Berge, et al., incorporated by reference herein in its entirety.

Compounds of formula (IV) can be prepared using methods described in International Patent Application Publication WO 00/71522, incorporated by reference herein in its entirety.

Compounds of formula (V) can be prepared using methods described in International Patent Application Publication WO 00/71524, incorporated by reference herein in its entirety.

The compounds of this invention are active against a range of important pathogenic bacteria, including Gram positive organisms, such as *Staphylococci*, for instance *S. aureus* Oxford and coagulase negative strains of *Staphylococci* such as *S. epidermidis*; *Streptococci*, for instance *S. pyogenes* CN10 and *S. pneumoniae* R6; and *Enterococci*, for instance *Ent. faecelis* I. Preferably, compounds of this invention are also active against Gram negative organisms, such as *Haemophilus*, for instance *H. influenzae* Q1; *Moraxella*, for instance *M. catarrhalis* 1502; and *Escherichia*, for instance *E. Coli* DC0. The most preferred compounds of the present invention will be active against the organisms *S. aureus*; *S. pneumoniae*; *Ent. faecelis*; *H. influenzae* and *M. catarrhalis*.

In addition, compounds of this invention are active against *Staphylococci* organisms such as *S. aureus* and coagulase negative strains of *Staphylocci* such as *S. epidermidis* which are resistant (including multiply-resistant) to other anti-bacterial agents, for instance, β-lactam antibiotics such as, for example, methicillin; macrolides; aminoglycosides, and lincosamides. Compounds of the present invention are therefore useful in the treatment of MRSA and MRCNS.

Compounds of the present invention are also active against strains of *E. faecalis* including vancomycin resistant strains and therefore of use in treating infections associated with VRE organisms. Furthermore, compounds of the present invention are useful in the treatment of *Staphylococci* organisms which are resistant to mupirocin.

Bacterial infections which may be treated include respiratory tract infections, otitis media, meningitis, endocarditis, skin and soft tissue infections in man, mastitis in cattle, and also respiratory infections in farm animals such as pigs and cattle. Accordingly, in a further aspect, the present invention provides a method of treating bacterial infection in human or non-human animals, which method comprises administering a therapeutically effective amount of a compound of formula (I) as hereinbefore defined, to a human or non-human animal in need of such therapy. It will be appreciated that a compound of the present invention which has a broad spectrum of anti-bacterial activity, including activity against both Gram positive and Gram negative bacteria will be of general use in the community for the empiric treatment of community acquired infections. In comparison, a compound of the present invention with a more limited spectrum, for instance activity against Gram positive bacteria, is more likely to be used in circumstances where the causative pathogenic organism has been identified.

The present invention provides a pharmaceutical composition comprising a compound of formula (I) together with a pharmaceutically acceptable carrier or excipient.

The present invention also provides a method of treating bacterial infections in animals, especially in humans and in domesticated mammals, which comprises administering a compound of formula (I), or a composition according to the invention, to a patient in need thereof.

The invention further provides the use of a compound of formula (I) in the preparation of a medicament composition for use in the treatment of bacterial infections.

The compounds and compositions according to the invention may be formulated for administration in any convenient way for use in human or veterinary medicine, by analogy with other antibiotics.

The compounds and compositions according to the invention may be formulated for administration by any route, for example oral, topical or parenteral. The compositions may, for example, be made up in the form of tablets, capsules, powders, granules, lozenges, creams, syrups, or liquid preparations, for example solutions or suspensions, which may be formulated for oral use or in sterile form for parenteral administration by injection or infusion.

Tablets and capsules for oral administration may be in unit dosage form, and may contain conventional excipients including, for example, binding agents, for example, syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, water being preferred. The compound, depending on the vehicle and concentration used, may be either suspended or dissolved in the vehicle. In preparing solutions, the compound may be dissolved in water for injection and filter-sterilised before being filled into a suitable vial or ampoule, which is then sealed. Advantageously, conventional additives including, for example, local anaesthetics, preservatives, and buffering agents can be dissolved in the vehicle. In order to enhance the stability of the solution, the composition may be frozen after being filled into the vial, and the water removed under vacuum; the resulting dry lyophilized powder may then be sealed in the vial and a accompanying vial of water for injection may be supplied to reconstitute the liquid prior to use. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

A compound or composition according to the invention may suitably be administered to the patient in an antibacterially effective amount.

A composition according to the invention may suitably contain from 0.1% by weight, preferably from 10 to 60% by weight, of a compound according to the invention (based on the total weight of the composition), depending on the method of administration.

The compounds according to the invention may suitably be administered to the patient at a daily dosage of from 1.0 to 100 mg/kg of body weight. For an adult human (of approximately 70 kg body weight), from 50 to 3000 mg, for example about 1500 mg, of a compound according to the invention may be administered daily. Suitably, the dosage for adult humans is from 5 to 20 mg/kg per day. Higher or lower dosages may, however, be used in accordance with normal clinical practice.

When the compositions according to the invention are presented in unit dosage form, each unit dose may suitably comprise from 25 to 1000 mg, preferable from 50 to 500 mg, of a compound according to the invention.

The following examples illustrate the activities of thiophenes sited in prior art U.S. Pat. No. 6,320,051.

| Prior Art Example | Structure | MIC *S. aureus* (ug/ml) | MIC *S. pneumo* (ug/ml) | MIC *H. influenzae* (ug/ml) |
|---|---|---|---|---|
| 37 | 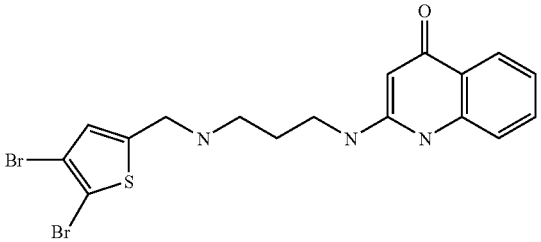 | 8 | 1 | >64 |
| 74 | 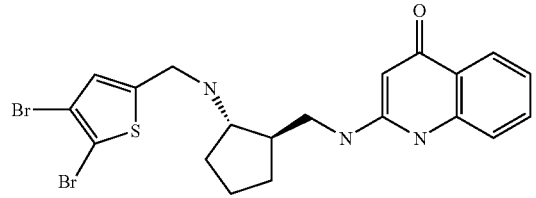 | 2 | 2 | >64 |
| 65 | 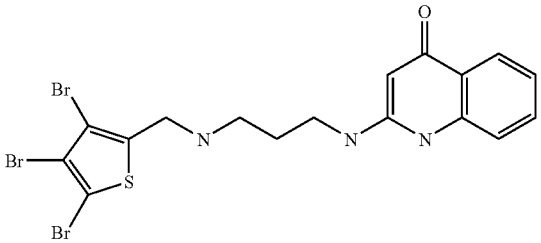 | 2 | 1 | >64 |
The following examples illustrate thiophenes with improved antibacterial activity that relate to the compounds of the present invention.
| Example # | Structure | MIC *S. aureus* (ug/ml) | MIC *S. pneumo* (ug/ml) | MIC *H. influenzae* (ug/ml) |
|---|---|---|---|---|
| 1 | 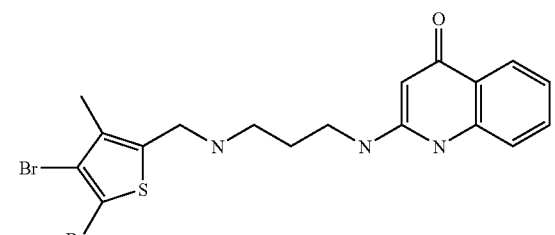 | 0.25 | 0.06 | 32 |
| 2 | 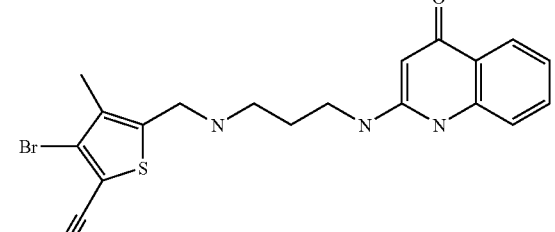 | 0.13 | 0.06 | >64 |

-continued

| Example # | Structure | MIC *S. aureus* (ug/ml) | MIC *S. pneumo* (ug/ml) | MIC *H. influenzae* (ug/ml) |
|---|---|---|---|---|
| 3 | 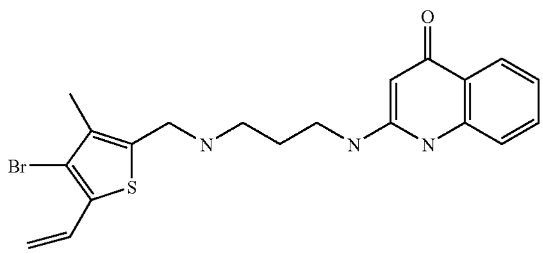 | 0.06 | 0.06 | 16 |
| 4 | 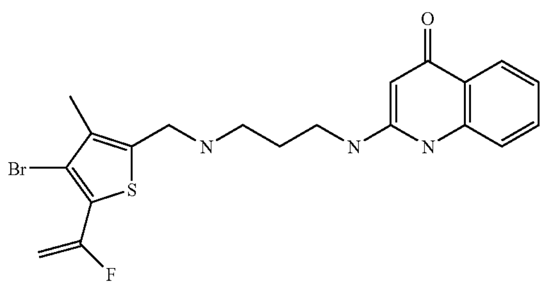 | 0.06 | 0.06 | 4 |
| 5 | 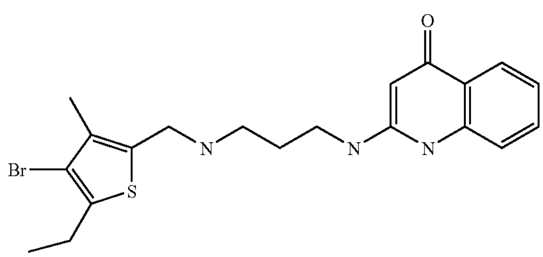 | 0.06 | 0.25 | 64 |
| 6 | 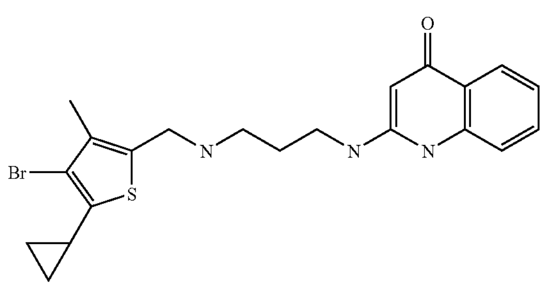 | 0.06 | 0.13 | 32 |
| 7 | 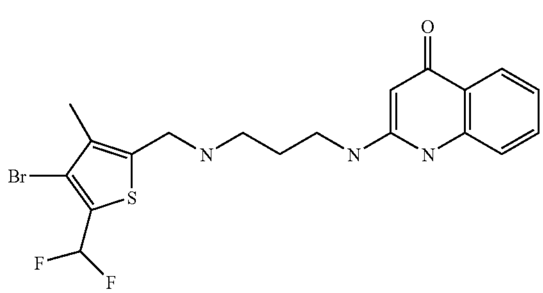 | 1 | 1 | 64 |

-continued

| Example # | Structure | MIC *S. aureus* (ug/ml) | MIC *S. pneumo* (ug/ml) | MIC *H. influenzae* (ug/ml) |
| --- | --- | --- | --- | --- |
| 8 | 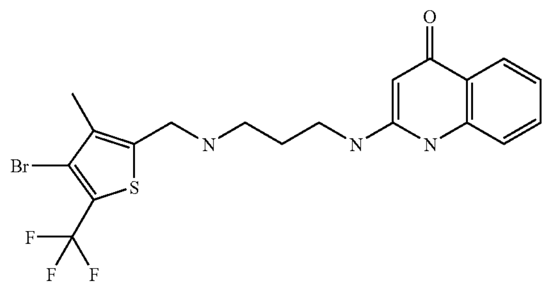 | 0.13 | 0.13 | 64 |
| 9 | 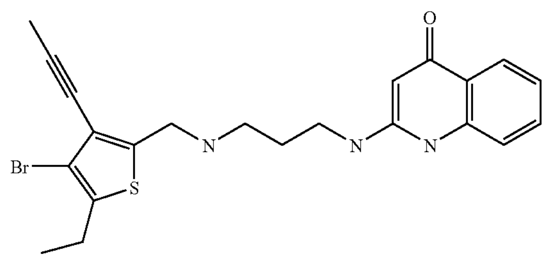 | 0.06 | 0.06 | 64 |
| 10 | 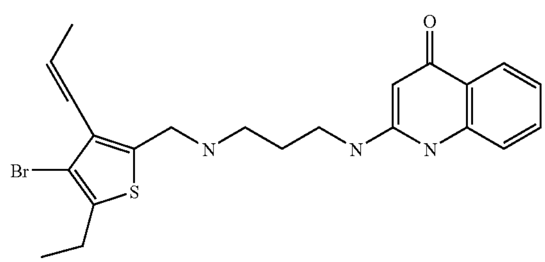 | 0.06 | .25 | 8 |
| 11 | 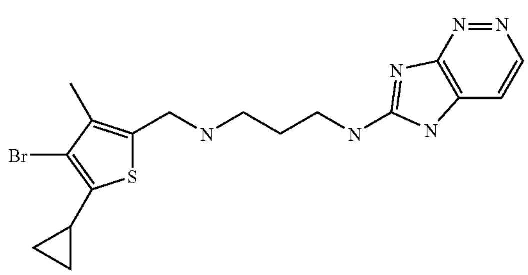 | 2 | 8 | 2 |
| 12 | 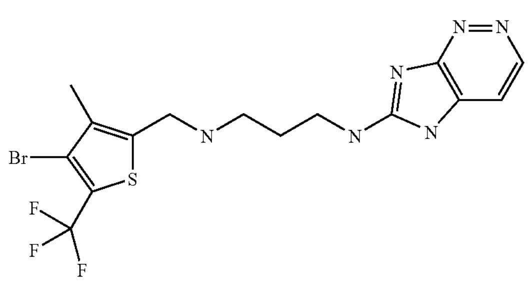 | 0.5 | 2 | 0.25 |

-continued

| Example # | Structure | MIC *S. aureus* (ug/ml) | MIC *S. pneumo* (ug/ml) | MIC *H. influenzae* (ug/ml) |
|---|---|---|---|---|
| 13 | 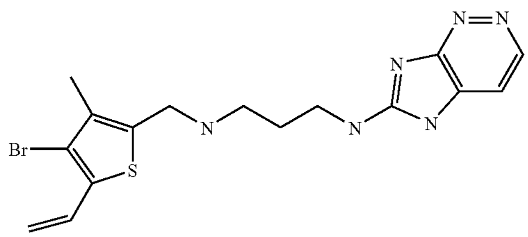 | 0.5 | 2 | 2 |
| 14 | 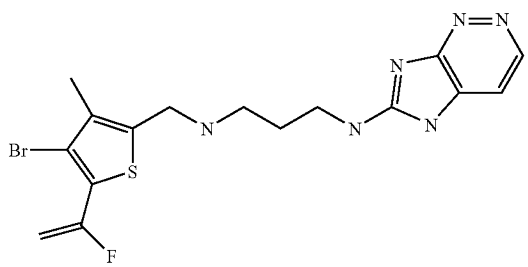 | 0.25 | 0.25 | 0.13 |
| 15 | 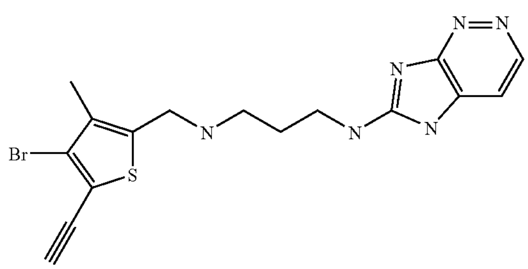 | 1 | 0.5 | 0.5 |
| 16 | 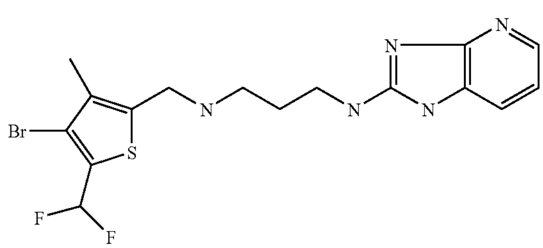 | 0.5 | 4 | 64 |
| 17 | 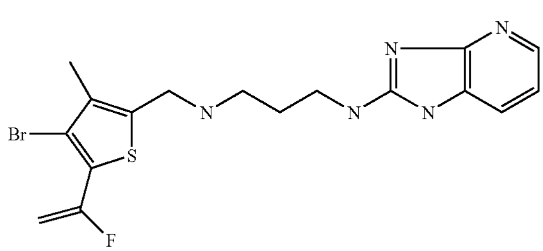 | 0.06 | 0.25 | 64 |
| 18 | 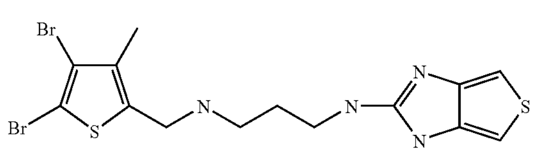 | 0.13 | 0.25 | 8 |

-continued

| Example # | Structure | MIC S. aureus (ug/ml) | MIC S. pneumo (ug/ml) | MIC H. influenzae (ug/ml) |
|---|---|---|---|---|
| 19 | *structure* | 0.13 | 0.5 | 16 |
| 20 | *structure* | 0.25 | 0.5 | 16 |
| 21 | *structure* | 0.06 | 0.25 | 8 |
| 22 | *structure* | 0.13 | 0.5 | 16 |
| 23 | *structure* | 1 | 4 | 8 |
| 24 | *structure* | 0.5 | 1 | 8 |
| 25 | *structure* | 0.5 | 2 | 32 |

General method for reductive amination To a suspension of the amine (0.2 mmol) (containing 0.5 mmol sodium acetate if the amine was present as the dihydrochloride) in methanol (2 ml) was added the aldehyde (0.2 mmol) in methanol (2 ml) and acetic acid (0.033 ml). After stirring under argon for 10 min, NaCNBH$_3$ (24 mg, 0.4 mmol) in MeOH (1 ml) was added and the reaction stirred for 16 h. The reaction mixture was applied to a 2 g Varian Bond Elute SCX cartridge which was flushed with MeOH (8 ml). The cartridge was then eluted with 8 ml 0.2 M NH$_3$ in MeOH, and this eluate evaporated to dryness. The residue was purified by chromatography on silica gel eluting with 2–10% (9:1 MeOH/20 M NH$_3$) in CH$_2$Cl$_2$. Product-containing fractions were combined and evaporated under reduced pressure to give the product as a white solid. To convert this into the corresponding dihydrochloride, the solid was dissolved in 1.0 M HCl in methanol (0.4 ml) and the solution evaporated to dryness.

EXAMPLE 1

N-(4,5-Dibromo-3-methylthiophen-2-ylmethyl)-N'-(1H-quinolin-4-one)propane-1,3-diamine Using the general method for reductive amination a mixture of 2-(3-aminoprop-1-ylamino)-1H-quinolin-4-one diamine 1a (J. Med. Chem. 2002, 45, 1959) and 4,5-dibromo-3-methylthiophene-2-carbaldehyde gave the title compound as a white solid (0.034 g, 49%). m/z (ES+) 484 (100% M+).

EXAMPLE 2

N-(4-bromo-5-ethynyl-3-methylthiophen-2-ylmethyl)-N'-(1H-quinolin-4-one)propane-1,3-diamine a) 4-Bromo-5-ethynyl-3-methylthiophene-2-carbaldehyde. A mixture of trimethylsilylacetylene (3.7 mL, 26.4 mmol), 4,5-dibromo-3-methylthiophene-2-carbaldehyde (1.50 g, 52.8 mmol), copper (I) iodide (19 mg) and bis(triphenylphosphine)palladium (II) chloride (80 mg) in triethylamine (35 mL) was stirred at room temperature. After 2 h the mixture was filtered and evaporated. The crude product was chromatographed over silica gel eluting with petroleum ether 40–60 containing increasing concentrations of dichloromethane up to 50%. The resultant trimethylsilyl protected acetylene was treated with methanol containing 10% concentrated ammonium hydroxide. After stirring at 20° C. for 15 minutes the solvent was evaporated to yield the title compound as a light brown foam (0.73 g); $\delta_H$ (CDCl$_3$) 9.99 (1H, s), 3.80 (1H, s), 2.55 (3H, s).

b) N-(4-bromo-5-ethynyl-3-methylthiophen-2-ylmethyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 2a gave the title compound as a white solid. m/z (ES+) 430 (100% M+).

EXAMPLE 3

N-(4-bromo-3-methyl-5-vinylthiophen-2-ylmethyl)-N'-(1H-quinolin-4-one)propane-1,3-diamine a) 4-Bromo-2-formyl-3-methyl-5-vinylthiophene.—In a 7 mL reaction tube under an inert atmosphere, 175 mg (0.616 mmol) of 4,5-dibromo-2-formyl-3-methylthiophene, 0.136 mL (0.616 mmol) of di-n-butoxyvinylborane, 199 mg (0.616 mmol) of tetra-nbutylammonium bromide, 213 mg (1.54 mmol) of potassium carbonate and 2.8 mg (0.012 mmol) of palladium acetate (added last) were dissolved in 1 mL of deionized water. The mixture was stirred vigorously at ambient temperature for 3 hours and then diluted with water and extracted with EtOAc (3×). The organic extracts and all non-aqueous soluble material were combined, activated charcoal was added and the mixture stirred for 10 minutes after which time it was filtered through celite and the solvent removed under reduced pressure to give yellowish crystals. These were then treated with refluxing hexane and activated charcoal, the hot hexane was filtered off through celite and the process repeated twice. The combined hexane extracts were evaporated to dryness to give 130 mg (87%, adjusted for contaminating starting material) of the title compound as a white solid (~15% contamination by thiophene starting material which can be removed by flash silica gel chromatography using CH$_2$Cl$_2$/Hexane as eluent). $\delta_H$ (CDCl$_3$) 2.5 (3H, s, CH$_3$), 5.49 (1H, dd, J=3.4, 11.0 Hz, CH$_2$), 5.89 (1H, dd, J=3.4, 17.4 Hz, CH$_2$), 6.95 (1H, dd, J=11.0, 17.4 Hz, CH), 10.00 (1H, s, CHO).

b) N-(4-bromo-5-vinyl-3-methylthiophen-2-ylmethyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 3a gave the title compound as a white solid. m/z (ES+) 432 (100% M+).

EXAMPLE 4

N-(4-bromo-5-(1-fluorovinyl)-3-methylthiophen-2-ylmethyl)-N'-(1H-quinolin-4-one)propane-1,3-diamine a) Diphenyl(1-fluorovinyl)methylsilane. In a flame-dried 1 L 3-neck round bottom under an anhydrous atmosphere, 65 mL (309 mmol) of diphenylmethylchlorosilane was added to 4.3 g (618 mmol) of lithium wire in 650 mL of anhydrous THF. The mixture was stirred at ambient temperature for 20 hours. The mixture was then cooled to −78° C. and the atmosphere replaced with 1,1-difluoroethylene (excess) such that the temperature of the reaction mixture remained below −55° C. Difluoroethylene addition was stopped when the reaction temperature remained at or below −70° C. The reaction was stirred at <−70° C. until it turned a clear light yellow (~2 hr.) and was then allowed to warm to ambient temperature. The remaining lithium wire was removed and the mixture treated with portions of Na$_2$SO$_4$-10H$_2$O until no gas evolved upon addition. The mixture was then dried over Na$_2$SO$_4$, filtered through a silica pad and the pad rinsed with ether. The combined filtrates were dried under vacuum, the resulting residue suspended/dissolved in hexanes and filtered through another silica pad. The pad was rinsed with hexanes, the filtrates combined and the solvent removed under reduced pressure to give a light yellowish liquid with some white crystalline material present. The product was purified by vacuum distillation (113–117° C. at ~2 Torr) to give 44 g (59%) of the title compound as a clear colorless liquid. $\delta_H$ (CDCl$_3$): 0.72 (3H, s, CH$_3$), 4.85 (1H, dd, J=2.6, 61.2 Hz, CH$_2$), 5.48 (1H, dd, J=2.6, 33.3, CH$_2$), 7.39 (6H, m, ArH), 7.59 (4H, d, J=6.8 Hz, ArH); $\delta_F$ (CDCl$_3$): −103.16 (q, dd, J=33.3, 61.2 Hz).

b) 4-Bromo-5-(1-fluorovinyl)-3-methylthiophene-2-carbaldehyde. Under an inert atmosphere in a 25 mL round bottom flask were combined 166 mg of 4a (0.685 mmol), 130 mg of 4,5-dibromo-3-methylthiophene-2-carbaldehyde (0.459 mmol), 209 mg of CsF (1.38 mmol), 88 mg of CuI (0.459 mmol), 10.5 mg Pd$_2$(dba)$_3$ (0.0115 mmol) and 14.1 mg AsPh$_3$ (0.0459 mmol). The flask containing the solids was cooled to ~0° C. with an ice bath and 2 mL of degassed, anhydrous dimethylformamide (DMF) were added. The reaction mixture was stirred at 0 to 5° C. for 2 hr and then 2 mL of water was added. The mixture was then diluted with 5 mL 1N NaOH and extracted with 25% diethyl ether/hexanes (4×20 mL). The combined extracts were washed with brine (1×5 mL), dried over Na$_2$SO$_4$, and the solvent removed under vacuum. The remaining residue was purified by flash silica gel chromatography (CH$_2$Cl$_2$/hexanes) to give a 50% yield of the title compound as a white solid. $\delta_H$ (CDCl$_3$) 2.57 (3H, s, CH$_3$), 5.24 (1H, dd, J=4.0, 18.5 Hz, CH$_2$), 5.70 (1H, dd, J=4.0, 49.6 Hz, CH$_2$), 10.06 (1H, s, CHO); $\delta_F$ (CDCl$_3$): −92.20 (q, dd, J=18.4, 50.4 Hz); m/z (ESI+) (MH+, 249).

c) N-(4-bromo-5-(1-fluorovinyl)-3-methylthiophen-2-yl-methyl)-N'-(1H-quinolin-4-one)propane-1,3-diamine.

Under a dry atmosphere and at ambient temperature, 1.00 g (3.45 mmol) of 2-(3-aminoprop-1-ylamino)-1H-quinolin-4-one dihydrochloride and 0.770 g (9.39 mmol) of NaOAc were dissolved in 40 mL of anhydrous MeOH and stirred for 10 min. at ambient temperature. 0.780 g of 4b (3.13 mmol) was then added followed by 8 mL of trimethylorthoformate and an additional 10 mL of anhydrous MeOH. The mixture was stirred at ambient temperature for 2 hr. The solvent was then removed under reduced pressure and the remaining residue was dissolved in 50 mL anhydrous MeOH and 0.474 g (12.5 mmol) of NaBH$_4$ was added at ambient temperature with stirring. After stirring for 30 min. at ambient temperature, the solvent was removed under reduced pressure and the resulting gummy solid was triturated with 0.1N NaOH (1×, stirring overnight required for product to solidify), deionized water (2×) and 1:1 Et$_2$O/Hexanes (2×). The remaining solid was dried under vacuum and the product purified by flash silica gel chromatography (NH$_3$ saturated MeOH/CH$_2$Cl$_2$) to give 900 mg (64%) of the desired product as a white foam. $\delta_H$ (CD$_3$OD/CDCl$_3$) 1.82 (2H, quin., J=6.4 Hz, CH$_2$), 2.15 (3H, s, CH$_3$), 2.74 (2H, t, J=6.4 Hz, CH$_2$), 3.33 (2H, t, J=6.8 Hz, CH$_2$), 3.92 (2H, s, CH$_2$), 4.94 (1H, dd, J=3.8, 18.6 Hz, CH$_2$), 5.33 (1H, dd, J=3.8, 50.6 Hz, CH$_2$), 5.58 (1H, s, CH), 7.18 (1H, d, J=8.0 Hz, ArH), 7.20 (1H, ddd, J=1.2, 7.1, 8.0, ArH), 7.45 (1H, ddd, J=1.4, 7.1, 8.3 Hz, ArH) 8.07 (1H, dd, J=1.2, 8.3 Hz, ArH); m/z (ESI$^+$) (MH$^+$, 450).

EXAMPLE 5

N-(4-bromo-5-ethyl-3-methylthiophen-2-ylmethyl)-N'-(1H-quinolin-4-one)propane-1,3-diamine a) 4-Bromo-5-ethynyl-3-methylthiophene-2-carbaldehyde. A mixture of trimethylsilylacetylene (3.7 mL, 26.4 mmol), 4,5-dibromo-3-methylthiophene-2-carbaldehyde (1.50 g, 52.8 mmol), copper (I) iodide (19 mg) and bis(triphenylphosphine)palladium (II) chloride (80 mg) in triethylamine (35 mL) was stirred at room temperature. After 2 h the mixture was filtered and evaporated. The crude product was chromatographed over silica gel eluting with petroleum ether 40–60 containing increasing concentrations of dichloromethane up to 50%. The resultant trimethylsilyl protected acetylene was treated with methanol containing 10% concentrated ammonium hydroxide. After stirring at 20° C. for 15 minutes the solvent was evaporated to yield the title compound as a light brown foam (0.73 g); $\delta_H$ (CDCl$_3$) 9.99 (1H, s), 3.80 (1H, s), 2.55 (3H, s).

b) 4-Bromo-3-methyl-5-ethyl-2-thiophenecarbaldehyde A mixture of 4-bromo-3-methyl-5-ethynyl-2-thiophenecarbaldehyde 5a (0.01 g, 0.44 mmol) and palladium on barium sulfate (0.008 g) in ethyl acetate (5 mL) was hydrogenated at atmospheric pressure and room temperature. After 3 h the mixture was filtered and the solvent evaporated to yield the desired product as a yellow oil. CIMS$^+$ 233 [MH$^+$].

c) N-(4-bromo-5-ethyl-3-methylthiophen-2-ylmethyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 5b gave the title compound as a white solid. m/z (ES+) 434 (100% M$^+$).

EXAMPLE 6

N-(4-bromo-5-cyclopropyl-3-methylthiophen-2-ylmethyl)-N'-(1H-quinolin-4-one)propane-1,3-diamine a) 4-Bromo-5-cyclopropyl-3-methyl-2-thiophenecarbaldehyde A suspension of 4,5-dibromo-3-methyl-2-thiophenecarbaldehyde (0.14 g, 0.55 mmol) and tetrakis(triphenylphosphino)palladium (0.02 g, 0.016 mmol) in DME (2 mL) was stirred at room temperature until an homogeneous solution formed (about 1 h). Cyclopropylboronic acid (0.05 g, 0.55 mmol) in aqueous sodium bicarbonate solution (0.123 g in 2 mL) was added and the resultant mixture stirred under reflux for 3 h. Cooled and diluted with ethylacetate/water. The organic phase was separated and aqueous phase extracted with a fresh portion of ethylacetate. The combined organic phases were dried and evaporated to yield the crude product.

b) 4-Bromo-5-ethyl-3-[(1E/Z)-1-propen-1-yl]-2-thiophenecarbaldehyde A mixture of 3,4-dibromo-5-ethyl-2-thiophenecarbaldehyde (0.25 g, 1 mmol), tributyl[(1E/Z)-1-propen-1-yl]stannane (0.397 g, 1.2 mmol), tetrakis(triphenylphosphino)palladium (0.124 g, 0.1 mmol) in toluene (5 mL) was heated at reflux. After 2 h the mixture was cooled, the solvent evaporated and the residue chromatographed over silica gel eluting with hexane containing an increasing concentration of dichloromethane (5 to 55%) to yield the title compound CIMS$_+$259 [MH$^+$].

EXAMPLE 7

N-(4-bromo-5-difluoromethyl-3-methylthiophen-2-ylmethyl)-N'-(1H-quinolin-4-one)propane-1,3-diamine a) 2-(4,5-Dibromo-3-methylthiophen-2-yl)-1,3-dioxolane. A solution of 4,5-dibromo-3-methylthiophene-2-carbaldehyde (2.84 g, 10 mmol), 1,2-dihydroxyethane (1.36 g, 22 mmol) and resin supported 4-toluenesulfonic acid in toluene (100 mL) was heated at reflux with separation of water. After 3 h the mixture was cooled, filtered and the solvent evaporated to yield the title compound (3.28 g); m/z (AP$^{+}$) 329 (MH$^+$, 100%).

b) 3-Bromo-5-(1,3-dioxolan-2-yl)-4-methylthiophene-2-carbaldehyde. Compound 7a (3.28 g, 10 mmol) was dissolved in dry THF (40 mL) and cooled to −78° C. under an argon atmosphere. A solution of n-butyl lithium (2.5 M in cyclohexane, 4 mL) was added dropwise. After stirring at −78° C. for 0.3 h, the solution was treated with dry DMF (0.775 mL, 10 mmol) and stirred for a further 0.6 h. The cooling bath was then removed and the solution allowed to reach room temperature over 3 h. The reaction mixture was quenched with 2N aqueous HCl and the product extracted into dichloromethane. The extracts were combined, dried (MgSO$_4$) and evaporated to yield the title compound (2.4 g); $\delta_H$ (CDCl$_3$) 2.29 (3H, s, CH$_3$), 4.07 (4H, m, CH$_2$CH$_2$), 6.14 (1H, s, CH), 9.98 (1H, s, CHO).

c) 2-(4-Bromo-5-difluoromethyl-3-methylthiophen-2-yl)-1,3-dioxolane. A solution of compound 7b (0.277 g, 1 mmol) and deoxofluor (0.378 g, 1.7 mmol) in dichloromethane (1 ml) was heated at reflux. After 14 h the mixture was diluted with dichloromethane, washed successively with aqueous sodium bicarbonate and 1N aqueous HCl, dried (MgSO$_4$) and evaporated to yield the title compound (0.28 g); $\delta_H$ (CDCl$_3$) 2.25 (3H, s, CH$_3$), 4.06 (4H, m, CH$_2$CH$_2$), 6.12 (1H, s, CH), 6.87 (1H, t, J=54.8 Hz, CHF$_2$).

d) 4-Bromo-5-difluoromethyl-3-methylthiophene-2-carbaldehyde. A solution of compound 7c (0.598 g, 2 mmol) and resin supported 4-toluenesulfonic acid in acetone (20 mL) containing water (1 mL) was stirred at room temperature. After 14 h the mixture was filtered and the solvent evaporated to yield the title compound (0.365 g); $\delta_H$ (CDCl$_3$) 2.56 (3H, s, CH$_3$), 6.90 (1H, t, J=56 Hz, CHF$_2$), 10.07 (1H, s, CHO).

e) N-(4-bromo-5-difluoromethyl-3-methylthiophen-2-yl-methyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 7d gave the title compound as a white solid. m/z (ES+) 456 (100% M$^+$).

EXAMPLE 8

N-(4-bromo-3-methyl-5-trifluoromethyl thiophen-2-ylmethyl)-N'-(1H-quinolin-4-one)propane-1,3-diamine a) 4-Bromo-3-methyl-5-trifluoromethylthiophene-2-carbaldehyde. 4,5-Dibromo-3-methylthiophene-2-carbaldehyde (250 mg, 0.88 mmol) was dissolved in a mixture of DMF (10 mL) and N-methylpyrrolidine (0.5 mL) containing copper (I) iodide (200 mg, 0.96 mmol) and 2,2-difluoro-2-fluorosulfonyl acetic acid methyl ester (871 mg, 4.4 mmol). After heating at 70° C. with vigorous stirring for 7 h the mixture was cooled and allowed to cool to room temperature overnight. The DMF was evaporated and the residue was partitioned between diethyl ether (30 mL) and saturated ammonium chloride solution. The organic layer was separated, washed with brine, dried and evaporated to yield the crude product. Filtration through silica gel eluting with hexane/diethyl ether (1:1) gave the title compound as a pale yellow solid (155 mg); m/z (AP$^-$) 272 (M$^-$, 25%).

b) N-(4-bromo-3-methyl-5-trifluoromethyl thiophen-2-yl-methyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 8a gave the title compound as a white solid. m/z (ES+) 474 (100% M$^+$).

EXAMPLE 9

N-(4-bromo-3-(1-propynyl)-5-ethyl thiophen-2-ylm-ethyl)-N'-(1H-quinolin-4-one)propane-1,3-diamine a) 3,4-Dibromo-5-ethylthiophene-2-carbaldehyde. 2,3,4-Tribromo-5-ethylthiophene (1.4 g, 4.1 mmol) was dissolved in dry THF (40 mL) and cooled to −78° C. under an argon atmosphere. A solution of n-butyl lithium (1.6 M in cyclohexane, 2.56 mL) was added dropwise. After stirring at −78° C. for 0.5 h, the solution was treated with dry DMF (0.32 mL, 4.1 mmol) and stirred for a further 0.6 h. The cooling bath was then removed and the solution allowed to reach room temperature over 3 h. The reaction mixture was quenched with 2M aqueous HCl and the product extracted into dichloromethane. The extracts were combined, dried (MgSO$_4$) and evaporated. The residue was chromatographed on Kieselgel 60 eluting with 0–50% dichloromethane in hexane to yield the title compound (0.6 g); m/z (AP$^+$) 299 (MH$^+$, 100%).

b) 4-Bromo-3-(1-propynyl)-5-ethylthiophene-2-carbaldehyde. Methyl acetylene was bubbled into a solution containing triethylamine (2 ml) and THF (2 ml). After 10 min the solution was quickly added to a 10 mL reactor vessel containing compound 9a (0.227 g, 0.8 mmol), bis(triphenylphosphine)palladium (II) chloride (5.8 mg, 0.008 mmol) and copper (I) iodide (0.15 mg, 0.0008 mmol). The reactor was sealed and the reaction mixture stirred at room temperature. After 60 h, the reaction mixture was filtered through celite and concentrated. The residue was chromatographed on Kieselgel 60 eluting with 0–50% dichloromethane in hexane to yield the title compound (0.126 g); m/z (AP$^+$) 257 (MH$^+$, 100%).

c) N-(4-bromo-3-(1-propynyl)-5-ethyl thiophen-2-ylm-ethyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 9b gave the title compound as a white solid. m/z (ES+) 458 (100% M$^+$).

EXAMPLE 10

N-(4-bromo-3-(1-propenyl)-5-ethyl thiophen-2-ylm-ethyl)-N'-(1H-quinolin-4-one)propane-1,3-diamine a) 3,4-Dibromo-5-ethyl-2-thiophenecarbaldehyde A solution of tetrabromothiophene (20 g, 50 mmol) in tetrahydrofuran (150 mL) was cooled to −78° C., under an atmosphere of argon, and treated dropwise with n-butyl lithium (20 mL of 2.5M in hexanes). After 20 mins the anion was quenched with iodoethane (4 mL, 50 mmol) and the resultant solution stirred at room temperature for 2 h. Reaction mixture cooled to −78° C. again and treated with another equivalent of n-butyl lithium. After a further 20 mins dry DMF (3.8 mL, 50 mmol) was added and the mixture allowed to warm to room temperature overnight. Water was added and the organic material extracted with dichloromethane, organic layer dried and evaporated to yield the crude product. Chromatography over silica gel eluting with hexane containing an increasing concentration of dichloromethane gave the title product as a pale yellow solid. CIMS$^+$ 297 [MH$^+$].

b) N-(4-bromo-5-cyclopropyl-3-methylthiophen-2-ylm-ethyl)-N'(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 6b gave the title compound as a white solid. m/z (ES+) 444 ( 100% M$^+$).Chromatography over silica gel eluting with petroleum ether/diethyl ether (0 to 25%) gave the title compound as a white crystalline solid. CIMS$^+$ 245 [MH$^+$].

c) N-(4-bromo-3-(1-propenyl)-5-ethyl thiophen-2-ylm-ethyl)-N'-(1H-quinolin-4-one)propane-1,3-diamine. Using the general method for reductive amination a mixture of 2-(3-aminoprop-1-ylamino)-1H-quinolin-4-one diamine 1a (J. Med. Chem. 2002, 45, 1959) and 10b gave the title compound as a white solid. m/z (ES+) 460 (100% M$^+$).

EXAMPLE 11

N-(4-Bromo-5-cyclopropyl-3-methylthiophen-2-ylmethyl)-N'-(5H-imidazo[4,5-c]pyridazin-6-yl)propane-1,3-diamine dihydrochloride a) [3-(5H-lmidazo[4,5-c]pyridazin-6-ylamino)propyl] carbamic acid t-butyl ester.

To a solution of 1,1'-thiocarbonyldiimidazole (1.34 g, 7.5 mmol) in tetrahydrofuran (10 mL) at 0° C. under an atmosphere of argon was added dropwise, over a 15 minute period, a solution of (3-aminopropyl)carbamic acid t-butyl ester (0.87 g, 5 mmol) in tetrahydrofuran (10 mL). After stiring at RT for 3 h the mixture was evaporated and dissolved in dry dimethylformamide (10 mL) and treated with 3,4-diaminopyridazine. The resultant mixture was heated under argon at 100° C. After 48 h the mixture was cooled and the DMF evaporated. Chromatography of the crude product over silica gel eluting with dichloromethane containing increasing concentrations of 10% ammonium hydroxide/methanol (0–12%) gave the title compound as a cream coloured solid. m/z (ES+) 293 (51%, MH$^+$).

b) N-(5H-Imidazo[4,5-c]pyridazin-6-yl)propane-1,3-diamine trifluoroacetate salt. [3-(5H-Imidazo[4,5-c]pyridazin-6-ylamino)propyl]carbamic acid t-butyl ester (0.27 g, 0.92 mmol) was treated with trifluoroacetic acid (2 mL) at RT. After 2 h the mixture was evaporated, dissolved in dichloromethane, re-evaporated and dried under vacuum to yield pale yellow foam.

c) N-(4-Bromo-5-cyclopropyl-3-methylthiophen-2-ylmethyl)-N'-(5H-imidazo[4,5-c]pyridazin-6-yl)propane-1,3-diamine dihydrochloride. Using the general method for reductive amination a mixture of N-(5H-Imidazo[4,5-c]pyridazin-6-yl)propane-1,3 -diamine 11b and 6a gave the title compound as a white solid. m/z (ES+) 460 (100% M$^+$).

EXAMPLE 12

N-(4-bromo-3-methyl-5-trifluoromethylthiophen-2-ylmethyl)-N'-(5H-imidazo[4,5-c]pyridazin-6-yl)propane-1,3-diamine dihydrochloride Using the general method for reductive amination a mixture of N-(5H-Imidazo[4,5-c]pyridazin-6-yl)propane-1,3-diamine 11b (and 8a gave the title compound as a white solid. m/z (ES+) 449 (100% M$^+$).

EXAMPLE 13

N-(4-bromo-3-methyl-5-vinylthiophen-2-ylmethyl)-N'-(5H-imidazo[4,5-c]pyridazin-6-yl)propane-1,3-diamine dihydrochloride Using the general method for reductive amination a mixture of N-(5H-Imidazo[4,5-c]pyridazin-6-yl)propane-1,3-diamine 11b and 3a gave the title compound as a white solid. m/z (ES+) 407 (100% M$^+$).

EXAMPLE 14

N-(4-bromo-5-(1-fluorovinyl)-3-methylthiophen-2-ylmethyl)-N'-(5H-imidazo[4,5-c]pyridazin-6-yl)propane-1,3-diamine dihydrochloride Using the general method for reductive amination a mixture of N-(5H-Imidazo[4,5-c]pyridazin-6-yl)propane-1,3-diamine 11b and 4b gave the title compound as a white solid. m/z (ES+) 425 (100% M$^+$).

EXAMPLE 15

N-(4-bromo-5-ethynyl-3-methylthiophen-2-ylmethyl)-N'-(5H-imidazo[4,5-c]pyridazin-6-yl)propane-1,3-diamine dihydrochloride Using the general method for reductive amination a mixture of N-(5H-Imidazo[4,5-c]pyridazin-6-yl)propane-1,3-diamine 11b and 2a gave the title compound as a white solid. m/z (ES+) 405 (100% M$^+$).

EXAMPLE 16

N-(4-bromo-5-difluoromethyl-3-methylthiophen-2-ylmethyl)-N'-(1H-imidazo[4,5-b]pyridin-2-yl)-propane-1,3-diamine a) 1,3-Dihydroimidazo[4,5-b]pyridine-2-thione To 2,3-diaminopyridine (4.36 g, 40 mmol) in pyridine (40 ml) was added carbon disulfide (3.6 ml, 60 mmol). The mixture was heated to 50° C. for 6 h then concentrated to low volume by evaporation under reduced pressure and the residue triturated with tetrahydrofuran. The pale brown solid was collected by filtration and dried to give a first crop of 3.6 g. A second crop (2.44 g) was obtained from the filtrate by re-evaporation and trituration with tetrahydrofuran. m/z (ESI+) 152 (MH$^+$, 100%).

b) 2-Methanesulfanyl-1H-imidazo[4,5-b]pyridine To compound 16a (5.55 g, 36.75 mmol) in dry tetrahydrofuran (100 ml) under argon was added triethylamine (5.66 ml, 40 mmol) and iodomethane (2.5 ml, 40 mmol). After stirring for 20 h at 20° C. the solid was removed by filtration and washed with THF. The combined filtrates were evaporated to dryness and triturated with dichloromethane. The solid was collected by filtration, (4.55 g, 75%). m/z (ESI+) 166 (MH$^+$, 100%).

c) N-(1H-imidazo[4,5-b]pyridin-2-yl)propane-1,3-diamine. The product from 16b (4.55 g) was treated with 1,3-diaminopropane (40 ml) at reflux under argon for 50 h. The solvent was removed by evaporation under reduced pressure and the residue triturated with diethyl ether to give a brown solid. This was purified by chromatography on silica gel eluting with 5–25% (9:1 methanol/0.880 aq. ammonia) in dichloromethane to give the required product, (2.6 g, 50%)

d) N-(4-bromo-5-difluoromethyl-3-methylthiophen-2-ylmethyl)-N'-(1H-imidazo[4,5-b]pyridin-2-yl)-propane-1,3-diamine. Using the general method for reductive amination a mixture of N-(1H-imidazo[4,5-b]pyridin-2-yl)propane-1,3-diamine 16c and 7d gave the title compound as a white solid. m/z (ES+) 430 (100% M$^+$).

EXAMPLE 17

N-(4-bromo-5-(1-fluorovinyl)-3-methylthiophen-2-ylmethyl)-N'-(1H-imidazo[4,5-b]pyridin-2-yl)-propane-1,3-diamine Using the general method for reductive amination a mixture of N-(1H-imidazo[4,5-b]pyridin-2-yl)propane-1,3-diamine 16c and 4b gave the title compound as a white solid. m/z (ES+) 424 (100% M$^+$).

EXAMPLE 18

N-(4,5-Dibromo-3-methylthiophen-2-ylmethyl)-N'-(1H-thieno[3,4-d]imidazol-2-yl)propane-1,3-diamine a) 3,4-Diaminothiophene. To a suspension of 2,5-dibromo-3,4-dinitrothiophene (10 g, 30.12 mmol) in conc. HCl (294 mL) was added portionwise tin (21.2 g, 178 mmol) keeping the temperature below 300° C. The mixture was stirred for 4 h at room temperature then stored in the fridge for two days. The solid was collected by filtration, washed with diethyl ether and acetone then suspended in water (60 mL) and diethylether (60 mL). The mixture was cooled in an ice-bath, then made alkaline using 4M NaOH. The aqueous phase was separated then continuously extracted with diethyl ether. The organic phases were combined then concentrated to give 2.3 g of the title compound as a beige solid; $\delta_H$ (CDCl$_3$) 6.1 (2H, s), 3.3 (4H, bs).

b) {3-[3-(4-Aminothiophen-3-yl)thioureido] propyl}carbamic acid tert-butyl ester. The product from 18a (0.421 g, 3.7 mmol) was dissolved in dichloromethane (13 mL) and treated with diisopropylethylamine (892 uL, 5.14 mmol), 4-dimethylaminopyridine (0.125 g, 1 mmol) and (3-isothiocyanato-propyl)carbamic acid tert-butyl ester (1.14 g, 5.28 mmol). The reaction mixture was stirred at room temperature for 16 h, loaded on Kieselgel 60 and chromatographed eluting with 0–2% (9:1 MeOH/20 M NH$_3$) in dichloromethane. The fractions containing the title compound were combined and concentrated, the residue was re-chromatographed on Kieselgel 60 eluting with 0–50% ethyl acetate in hexane. The fractions containing the title compound were combined and concentrated, the residue was applied to a 10 g Varian Bond Elute SCX cartridge which was flushed with methanol. The cartridge was then eluted with 0.2 M NH$_3$ in methanol, and this eluate evaporated to dryness to afford the title compound as a pale yellow oil (0.26 g, 21%), m/z (CI$^+$) 331 (MH$^+$, 10%).

c) [3-(1H-Thieno[3,4-d]imidazol-2-ylamino)propyl]carbamic acid tert-butyl ester. The product from 18b (0.180 g, 0.54 mmol) was dissolved in dimethylformamide (40 mL) and treated with triethylamine (76 uL, 0.54 mmol) and mercuric chloride (0.149 g, 0.54 mmol). The reaction mixture was stirred at room temperature for 16 h then diluted with ethyl acetate and filtered through celite. The filtrate was concentrated and the residue chromatographed on Kieselgel 60 eluting with 0–10% (9:1 MeOH/20 M NH$_3$) in CH$_2$Cl$_2$ to afford the title compound as a brown oil (0.050 g, 31%), m/z (CI$^+$) 297 (MH$^+$, 100%).

d) N-(1H-Thieno[3,4-d]imidazol-2-yl)propane-1,3-diamine bistrifluoroacetate salt. The product from 18c (0.045 g, 0.15 mmol) was dissolved in trifluoroacetic acid (2 mL). The reaction mixture was stirred at room temperature for 0.5 h then concentrated to afford the title compound as a brown oil (0.056 g, 88%), m/z (CI$^+$) 197 (MH$^+$, 80%),393 (2 MH$^+$, 100%).

e) N-(4,5-Dibromo-3-methylthiophen-2-ylmethyl)-N'-(1H-thieno[3,4-d]imidazol-2-yl)propane-1,3-diamine. The product from 18d was coupled to 4,5-dibromo-3-methylthiophene-2-carbaldehyde on a 0.09 mmol scale using the general method for reductive amination to give the title compound as a pink solid (0.015 g, 36%), m/z (CI$^+$) 465 (MH$^+$, 100%).

EXAMPLE 19

N-(4-Bromo-5-difluoromethyl-3-methylthiophen-2-ylmethyl)-N'-(1H-thieno[3,4-d]imidazol-2-yl)propane-1,3-diamine Using the general method for reductive amination a mixture of N-(1H-imidazo[4,5-b]pyridin-2-yl)propane-1,3-diamine 18d and 7d gave the title compound as a white solid. m/z (ES+) 435 (100% M$^+$).

EXAMPLE 20

N-(4-Bromo-3-methyl-5-trifluoromethylthiophen-2-ylmethyl)-N'-(1H-thieno[3,4-d]imidazol-2-yl)propane-1,3-diamine Using the general method for reductive amination a mixture of N-(1H-imidazo[4,5-b]pyridin-2-yl)propane-1,3-diamine 18d and 8a gave the title compound as a white solid. m/z (ES+) 453 (100% M$^+$).

EXAMPLE 21

N-(4-bromo-5-(1-fluorovinyl)-3-methylthiophen-2-ylmethyl)-N'-(1H-thieno[3,4-d]imidazol-2-yl)propane-1,3-diamine Using the general method for reductive amination a mixture of 18d and 4b gave the title compound as a white solid. m/z (ES+) 429 (100% M$^+$).

EXAMPLE 22

N-(4-bromo-5-(1-fluorovinyl)-3-methylthiophen-2-ylmethyl)-N'-(1H-benzimidazole)propane-1,3-diamine a) 2-(3-Aminopropylamino)benzimidazole. 2-Chloro-1H-benzimidazole 1.53 g, 10 mmol) and 1,3 diamionpropane (25 ml, 300 mmol) were heated together for 18 h at 90 C, then at 120 C for 72 h. The solution was evaporated to dryness, then triturated with dichloromethane to afford a pale brown powder. This powder was dissolved in methanol and pre-absorbed onto silica. Flash chromatography, eluting with 1% ammonia in methanol and dichloromethane, gave the title compound as a powder (1.45 g, 76%); $\delta_H$ (CD$_3$OD) 1.73 (2H, quintet), 2.69 (2H, t), 3.34 (2H, t), 6.82–6.92 (2H, m), and 7.04–7.13 (2H, m); LC/MS (ES+) 191 (100%, MH+)

b) N-(4-bromo-5-(1-fluorovinyl)-3-methylthiophen-2-ylmethyl)-N'-(1H-benzimidazole)propane-1,3-diamine. Using the general method for reductive amination a mixture of 2-(3-Aminopropylamino)benzimidazole 22a and 4b gave the title compound as a white solid. m/z (ES+) 423 (100% M$^+$).

EXAMPLE 23

N-(4-bromo-5-difluoromethyl-3-methylthiophen-2-ylmethyl)-N'-(1H-benzimidazole)propane-1,3-diamine Using the general method for reductive amination a mixture of 2-(3-Aminopropylamino)benzimidazole 22a and 7d gave the title compound as a white solid. m/z (ES+) 429 (100% M$^+$).

EXAMPLE 24

N-(4-bromo-3-methyl-5-trifluoromethylthiophen-2-ylmethyl)-N'-(1H-benzimidazole)propane-1,3-diamine Using the general method for reductive amination a mixture of 2-(3-Aminopropylamino)benzimidazole 22a and 8a gave the title compound as a white solid. m/z (ES+) 447 (100% M$^+$).

EXAMPLE 25

N-(4,5-Dibromo-3-methylthiophen-2-ylmethyl)-N'-(1H-thieno [3,2-d]pyrimidin-4-one)propane-1,3-diamine a) Potassium 1H-thieno[3,2-d]pyrimidin-4-one-2-thiolate-3-(3-Benzoylthioureido)-2-thiophenecarboxylic acid methyl ester (75 g; Gutschow, J. Het. Chem. 1996, 33, 355–360) was added to a solution of KOH (25 g) in ethanol (1 L) and heated to reflux for 2.5 hours. A lemon colored solid was filtered off to yield the title compound of about 85% purity which was used without further purification in the next step: (46 g). $\delta_H$ (d6-DMSO) 6.87 (m, 1H), 7.22 (m, 1H), 10.35 (br, 1H) plus benzoate impurity.

b) 2-Methylsulfanyl-1H-thieno [3,2-d]pyrimidin-4-one-Potassium 1H-thieno[3,2-d]pyrimidin-4-one-2-thiolate (46 g) of about 85% purity was added to water (1 l). Methyl iodide (1 3 ml) was added and the mixture was stirred for 3 h. A white precipitate was filtered off and dried to yield the title compound as an off-white solid: (30 g, 82%). $\delta_H$ (d6-DMSO) 2.55 (s, 3H), 7.3 1 (d, J=5.2 Hz, 1H), 8.13 (d, J=5.2 Hz, 1H), 12.78 (br, 1H).

c) 2-(3-Aminopropylamino)-1H-thieno [3,2–4 pyrimidin-4-one. 2-Methylsulfanyl-1H-thieno[3,2-d]pyrimidin-4-one (20 g) was treated with 1,3-diaminopropane (104 ml) and heated in a sealed vessel to 140 C for 48 h. After cooling, a yellow crystalline solid was filtered off. The remaining reaction mixture was concentrated in vacuo, triturated with methanol, and purified by column chromatography. The crystals and the material obtained from chromatography were combined to yield the title compound: (8.0 g, 35%). $\delta_H$ (d6-DMSO) 1.96 (m, 2H), 2.96 (m, 2H), 3.69 (m, 2H), 5.16 (br, ca. 4H under H$_2$O peak), 7.54 (d, J=5, 1H), 8.28 (d, J=5, 1H).

d) N-(4,5-Dibromo-3-methylthiophen-2-ylmethyl)-N'-(1H-thieno [3,2-d]pyrimidin-4-one)propane-1,3-diamine. Using the general method for reductive amination a mixture of 2-(3-Aminopropylamino)-1H-thieno [3,2–4 pyrimidin-4-one 25c and 4,5-dibromo-3-methylthiophene-2-carbaldehyde gave the title compound as a white solid (0.034 g, 49%). m/z (ES+) 492 (100% M$^+$).

Biological Data

1. Enzyme Inhibition (*S. aureus* MRS)—aminoacylation assay

Compounds of the present invention may be assayed for their ability to inhibit the enzyme methionyl tRNA synthetase (MRS), using recombinant *S. aureus* MRS, as follows:

Reaction Mix (per 1 ml)

| Stock | Volume (μl) | Final Concentration |
| --- | --- | --- |
| 100 mM Tris/Cl, pH 7.9 | 600 | 30 mM |
| 250 mM KCl |  | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 40 | 10 uM |
| Solid tRNA (Mixed *E. coli* MRE 600) | 4 mg/ml | 2 mg/ml |
| H$_2$O | 160 |  |
| 10 × Inhibitor (0–10 μM) | 5 μl per well | 0–1 μM |

The reaction is started by adding 20 ul appropriately diluted pure enzyme (pre-incubated with inhibitor) to 25 μl reaction mix for 10 min at room temperature. The reaction is terminated by the addition of 150 μl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed *E. coli* MRE 600 tRNA and ATP were purchased from Boehringer-Mannheim, L-[methyl-$^3$H]methionine and phosphodiesterase scintillation proximity (SPA) beads from Amersham Pharmacia Biotech and other reagents from Signia.

Pure recombinant *S. aureus* MRS (EP application number 97300317.1, SmithKline Beecham) was obtained using standard purification procedures. The enzyme is diluted in Dilution Buffer which consists of 10 mM Tris/Cl, 2 mM DTT pH 7.9.

Results

Examples 1 to 25 have IC$_{50}$ values against *S. aureus* MRS in the range <3 to 200 nM. All are highly selective with respect to the mammalian enzyme (no inhibition of rat MRS up to 1 μM).

2. Enzyme Inhibition (*H. influenzae* MRS)—aminoacylation assay

Compounds of the present invention may be assayed for their ability to inhibit the enzyme methionyl tRNA synthetase (MRS), using recombinant *H. influenzae* MRS(R. D. Fleischmann et al., Science, 269, 496–512, 1995), as follows:

| Stock | Volume (μl) | Final Concentration |
| --- | --- | --- |
| 100 mM Tris/Cl, pH 7.9 | 600 | 30 mM |
| 250 mM KCl |  | 75 mM |
| 125 mM ATP | 40 | 2.5 mM |
| 250 mM MgCl$_2$ | 80 | 10 mM |
| 50 mM DTT | 80 | 2 mM |
| 1 mM Met (H-3 hot and cold) | 20 | 10 μM |
| Solid tRNA (Mixed *E. coli* MRE 600) | 4 mg/ml | 2 mg/ml |
| H$_2$O | 180 |  |
| 10 × Inhibitor (0–100 μM) | 5 μl per well | 0–10 μM |

The reaction is started by adding 20 μl appropriately diluted pure enzyme (pre-incubated with inhibitor) to 25 μl reaction mix for 10 min at room temperature. The reaction is terminated by the addition of 150 μl 167 mM sodium citrate, pH 2.15 containing phosphodiesterase (PDE) SPA beads (0.833 mg/ml). The binding of the radiolabelled product to the bead brings the isotope into close enough proximity to allow radiation from the tritium to excite the scintillant within the bead. Any unbound radiolabel is not close enough to the scintillant to allow this energy transfer, so no signal is generated. Following termination of the reaction, plates are spun at 2500 rpm for 5 min in a Mistral 3000E plate centrifuge (or alternatively allowed to stand for 1 hour). The assay is conducted in 96-well Optiplates (Packard). Plates are counted on a TopCount. (Packard 96 well counter).

Reagents

Mixed *E. coli* MRE 600 tRNA and ATP were purchased from Boehringer-Mannheim, L-[methyl-$^3$H]methionine and phosphodiesterase scintillation proximity (SPA) beads from Amersham Pharmacia Biotech and other reagents from Sigma.

Results

Examples 1–8, 11–15, 17, 18, 21, 22, 25 have $IC_{50}$ values against *H. influenzae* MRS in the range <3 to 200 nM. All are highly selective with respect to the mammalian enzyme (no inhibition of rat MRS up to 1 μM).

3. Antibacterial Activity

Compounds of the present invention were assayed for antibacterial activity against a range of pathogenic organisms (strains of *S aureus, S pneumoniae, E faecalis, H influenzae* and *M catarrhalis*) in a standard MIC assay modified by the inclusion of cyclodextrin, to assist with solubility.

Examples 1–6, 8–10, 12–14, 16–22, 24, 25 had MIC's 0.06–0.50 μg/ml against some strains of the organisms *S. aureus, S. pneumoniae*, and *E. faecalis*. This is an unexpected improvement in potency against the major gram positive pathogens by a multiple of between 10–50 when compared to the thiophenes in the prior art. Examples 7, 11, 15 and 23 had MIC's 1–2 μg/ml against some strains of the organisms *S. aureus, S. pneumoniae*, and *E. faecalis*. Examples 4, 10–15, 18, 21, 23, 24 had MIC's 0.13–8 μg/ml against some strains of the organisms *M catarrhalis* and *H. influenzae*. This is an unexpected improvement in potency against these two major gram negative pathogens by a multiple of between 10–500 when compared to the thiophenes in the prior art.

What is claimed is:

1. A compound of the formula (I):

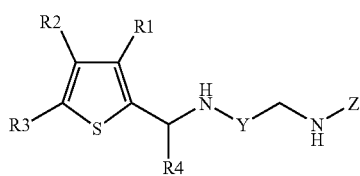

(I)

in which

R$^1$ is selected from the group consisting of C$_{(1-3)}$ alkyl, C$_{(2-3)}$ alkenyl, C$_{(2-3)}$ alkynyl;

R$^2$ is halogen;

R$^3$ is selected from the group consisting of Br, optionally fluoro-substituted C$_{(1-3)}$ alkyl, optionally fluoro-substituted C$_{(2-3)}$ alkenyl, and C$_{(2-3)}$ alkynyl;

R$^4$ is selected from the group consisting of H, and C$_{(1-3)}$ alkyl;

Y is C$_{(1-3)}$ alkyl; and

Z is substituted or unsubstituted quinolone.

2. A compound according to claim 1, wherein the compound is a compound of the formula (III):

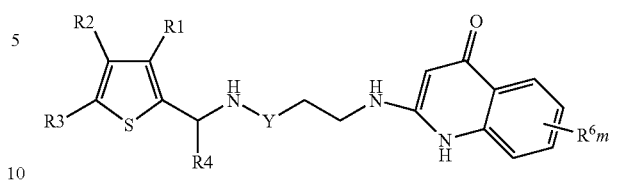

(III)

in which:

R$^1$, R$^2$, R$^3$, R$^4$ and Y are defined as in claim 1; and

R$^6$ is selected from the group consisting of halo, cyano, hydroxy, (C$_{1-6}$)alkyl, optionally substituted by a member selected from the group consisting of halo, hydroxy, amino, mono to perfluoro(C$_{1-3}$)alkyl, carboxy or (C$_{1-6}$)alkoxycarbonyl), (C$_{3-7}$)cycloalkyl, C$_{(1-6)}$ alkoxy, amino, mono- or di-(C$_{1-6}$)alkylamino, acylamino, carboxy, (C$_{1-6}$)alkoxycarbonyl, carboxy(C$_{1-6}$)alkyloxy, (C$_{1-6}$)alkylthio, (C$_{1-6}$)alkylsulphinyl, (C$_{1-6}$)alkylsulphonyl, sulphamoyl, mono- and di-(C$_{1-6}$)alkylsulphamoyl, carbamoyl, mono- and di-(C$_{1-6}$)alkylcarbamoyl, and heterocyclyl;

m is 0 or an integer from 1 to 3.

3. A compound according to claim 1, in which:

R$^1$ is selected from the group consisting of methyl, allyl, propene, and propyne;

R$^2$ is Br;

R$^3$ is selected from the group consisting of Br, ethyl, cyclopropyl, difluoromethyl, trifluoromethyl, vinyl, fluorovinyl, and ethyne;

R$^4$ is H;

Y is C$_2$ alkyl; and

Z is quinoline.

4. A salt of a compound according to claim 1.

5. The salt of claim 4, wherein the salt is a pharmaceutically acceptable salt.

6. The compound of claim 1, wherein the compound is selected from the group consisting of N-(4,5-Dibromo-3-methylthiophen-2-ylmethyl)-N'-(1H-quinolin-4-one)propane-1,3-diamine;

N-(4-bromo-5-ethynyl-3-methylthiophen-2-ylmethyl)-N'-(1H-quinolin-4-one)propane-1,3-diamine;

N-(4-bromo-3-methyl-5-vinylthiophen-2-ylmethyl)-N'-(1H-quinolin-4-one)propane-1,3-diamine;

N-(4-bromo-5-(1-fluorovinyl)-3-methylthiophen-2-ylmethyl)-N'-(1H-quinolin-4-one)propane-1,3-diamine;

N-(4-bromo-5-ethyl-3-methylthiophen-2-ylmethyl)-N'-(1H-quinolin-4-one)propane-1,3-diamine;

N-(4-bromo-5-cyclopropyl-3-methylthiophen-2-ylmethyl)-N'-(1H-quinolin-4-one)propane-1,3-diamine;

N-(4-bromo-5-difluoromethyl-3-methylthiophen-2-ylmethyl)-N'-(1H-quinolin-4-one)propane-1,3-diamine;

N-(4-bromo-3-methyl-5-trifluoromethyl thiophen-2-ylmethyl)-N'-(1H-quinolin-4-one)propane-1,3-diamine;

N-(4-bromo-3-(1-propynyl)-5-ethyl thiophen-2-ylmethyl)-N'-(1H-quinolin-4-one)propane-1,3-diamine; and N-(4-bromo-3-(1-propenyl)-5-ethyl thiophen-2-ylmethyl)-N'-(1H-quinolin-4-one)propane-1,3-diamine.

7. A pharmaceutical composition comprising a compound or salt of claim 1 and a pharmaceutically acceptable carrier or excipient.

8. A compound according to claim 2 in which:
R$^1$ is selected from the group consisting of methyl, allyl, propene, and propyne;
R$^2$ is Br;
R$^3$ is selected from the group consisting of Br, ethyl, cyclopropyl, difluoromethyl, trifluoromethyl, vinyl, fluorovinyl, and ethyne;
R$^4$ is H;
Y is C$_2$ alkyl; and
Z is quinolone.

9. A pharmaceutical composition comprising a compound or salt of claim 2 and a pharmaceutically acceptable carrier or excipient.

10. A salt of a compound according to claim 2.

11. The salt of claim 8, wherein the salt is a pharmaceutically acceptable salt.

12. A salt of a compound according to claim 1, in which,
R$^1$ is selected from the group consisting of methyl, allyl, propene, and propyne;
R$^2$ is Br;
R$^3$ is selected from the group consisting of Br, ethyl, cyclopropyl, difluoromethyl, trifluoromethyl, vinyl, fluorovinyl, and ethyne;
R$^4$ is H;
Y is C$_2$ alkyl; and
Z is quinolone.

13. A salt of a compound according to claim 2, in which,
R$^1$ is selected from the group consisting of methyl, allyl, propene, and propyne;
R$^2$ is Br;
R$^3$ is selected from the group consisting of Br, ethyl, cyclopropyl, difluoromethyl, trifluoromethyl, vinyl, fluorovinyl, and ethyne;
R$^4$ is H;
Y is C$_2$ alkyl; and
Z is quinolone.

14. The salt of claim 13, wherein the salt is a pharmaceutically acceptable salt.

15. A method of treating a bacterial infection, comprising administering a compound of claim 1 to a patient in need thereof.

16. A method of treating a bacterial infection, comprising administering a compound of claim 2 to a patient in need thereof.

17. A method of treating a bacterial infection, comprising administering a compound of claim 3 to a patient in need thereof.

18. A method of treating a bacterial infection, comprising administering a compound of claim 4 to a patient in need thereof.

19. A method of treating a bacterial infection, comprising administering a compound of claim 5, to a patient in need thereof.

20. A method of treating a bacterial infection, comprising administering a compound of claim 6 to a patient in need thereof.

21. A method of treating a bacterial infection, comprising administering a compound of claim 8 to a patient in need thereof.

22. A method of treating a bacterial infection, comprising administering a composition of claim 9 to a patient in need thereof.

23. A method of treating a bacterial infection, comprising administering a compound of claim 10 to a patient in need thereof.

24. A method of treating a bacterial infection, comprising administering a compound of claim 11 to a patient in need thereof.

25. A method of treating a bacterial infection, comprising administering a compound of claim 13 to a patient in need thereof.

26. A method of treating a bacterial infection, comprising administering a compound of claim 13 to a patient in need thereof.

27. A method of treating a bacterial infection, comprising administering a compound of claim 14 to a patient in need thereof.

* * * * *